United States Patent
Mühlhoff et al.

(10) Patent No.: US 8,425,494 B2
(45) Date of Patent: Apr. 23, 2013

(54) ADAPTER FOR MECHANICALLY COUPLING A LASER PROCESSING DEVICE TO AN OBJECT

(75) Inventors: Dirk Mühlhoff, Kunitz (DE); Elke Ebert, Jena (DE); Karsten Festag, Jena (DE); Uwe Wolf, Magdala (DE)

(73) Assignee: Carl Zeiss Meditec AG, Jena (DE)

( * ) Notice: Subject to any disclaimer, the term of this patent is extended or adjusted under 35 U.S.C. 154(b) by 908 days.

(21) Appl. No.: 10/579,645

(22) PCT Filed: Nov. 16, 2004

(86) PCT No.: PCT/EP2004/012998
§ 371 (c)(1),
(2), (4) Date: May 21, 2007

(87) PCT Pub. No.: WO2005/048895
PCT Pub. Date: Jun. 2, 2005

(65) Prior Publication Data
US 2007/0237620 A1    Oct. 11, 2007

(30) Foreign Application Priority Data
Nov. 19, 2003  (DE) ................................. 103 54 025

(51) Int. Cl.
*A61B 18/18*    (2006.01)
(52) U.S. Cl.
USPC .......................................... 606/4; 414/751.1
(58) Field of Classification Search .................. None
See application file for complete search history.

(56) References Cited

U.S. PATENT DOCUMENTS

| | | | |
|---|---|---|---|
| 4,718,418 A | 1/1988 | L'Esperance, Jr. | |
| 4,905,711 A | 3/1990 | Bennett et al. | |
| 5,336,215 A * | 8/1994 | Hsueh et al. | 606/4 |
| 5,549,632 A | 8/1996 | Lai | |
| 5,656,186 A | 8/1997 | Mourou et al. | |
| 5,984,916 A | 11/1999 | Lai | |
| 6,254,595 B1 | 7/2001 | Juhasz et al. | |
| 6,373,571 B1 | 4/2002 | Juhasz et al. | |
| 7,357,504 B2 * | 4/2008 | Fischer et al. | 351/200 |
| 2001/0021844 A1 | 9/2001 | Kurtz et al. | |
| 2002/0103482 A1 | 8/2002 | Scholler et al. | |

FOREIGN PATENT DOCUMENTS

| | | |
|---|---|---|
| DE | 198 31 674 | 1/2000 |
| DE | 198 31 674 A1 | 1/2000 |
| EP | 0 336 065 A2 | 10/1989 |
| EP | 1 159 986 A2 | 12/2001 |
| WO | WO 03/002008 | 1/2003 |
| WO | WO 03/002008 A1 | 1/2003 |

* cited by examiner

Primary Examiner — Saul Rodriguez
Assistant Examiner — Willie Berry, Jr.
(74) Attorney, Agent, or Firm — Patterson Thuente Pedersen, P.A.

(57) ABSTRACT

An adapter for mechanically coupling a laser processing device to an object. The adapter has a central region which can be moved into the beam path of the laser processing device and a peripheral region located outside the central region. The beam path extends up to the object along an optical axis. The adapter is fixable to the laser processing device on the one hand and provided so as to contact the object with its central region on the other hand. A fixture is provided at the peripheral region that allows the adapter to be releasably fixed to a receiving part of the laser processing device such that, upon application of a determined pulling force along the optical axis, the The fixture is removable from the receiving part.

20 Claims, 4 Drawing Sheets

ADAPTER FOR MECHANICALLY COUPLING A LASER PROCESSING DEVICE TO AN OBJECT

FIELD OF THE INVENTION

The invention relates to an adapter for mechanically coupling a laser processing device to an object, said adapter comprising a central region which can be switched into the beam path of the laser processing device, which beam path extends up to the object along an optical axis, and which adapter comprises a peripheral region located outside the central region and is fixable to the laser processing device on the one hand and being provided so as to contact the object with its central region on the other hand.

BACKGROUND OF THE INVENTION

In materials processing, a laser processing device is often employed for scanning the areas of the object which are to be processed with a laser beam. The precision in positioning the laser beam usually determines the precision achieved in processing. Exact three-dimensional positioning is required when focusing the laser beam into a processing volume. For high-precision processing, it is usually indispensable, therefore, to hold the object in an exactly defined position relative to the laser processing device. For such applications, the above-mentioned adapter is useful, because it enables fixation of the object to be processed, so that defined ratios can be achieved up to the processing volume. The central region of the adapter thus becomes part of the beam path.

This is necessary, in particular, in micro-processing of materials which have only low linear optical absorption in the spectral range of the processing laser radiation. In such materials, usually non-linear interactions between the laser radiation and the material are utilized generally in the form of an optical breakthrough being generated in the focus of the laser beam. Since the processing effect then only occurs in the laser beam focus, exact three-dimensional positioning of the focal point is indispensable. Thus, exact depth adjustment of the focal position in the beam path is required in addition to two-dimensional deflection of the laser beam. The above-mentioned adapter serves to ensure constant optical conditions and ones that are known with a certain precision in the beam path leading to the object due to the central region of the adapter being part of the beam path and the adapter coupling the object and the laser processing device.

A typical application for such an adapter is the ophthalmic method known as femtosecond LASIK, wherein the laser processing device provided as a therapeutic appliance focuses a laser beam to a focal point on the order of a few micrometers into the cornea. A plasma causing local separation of the corneal tissue is then generated in the focus. By suitable sequential arrangement of the zones of local separation thus generated, macroscopic cuts are realized and a determined partial volume of the cornea is isolated. Then, by removal of said partial volume, a desired change in refraction of the cornea is achieved, thus enabling correction of defective eyesight.

In connection with the LASIK method, a contact lens provided with reference marks is known from U.S. Pat. No. 6,373,571. This contact lens is adjusted by means of a separate measurement device, causing a relatively complex design. An example of an adapter of the aforementioned type is described in EP 1,159,986 A2. While being similar to the contact lens of U.S. Pat. No. 6,373,571, it additionally comprises a periphery in the form of a holder having line marks, which allow visual alignment by the surgeon.

In materials processing by means of laser radiation, there often arises the need to monitor execution of processing. It is desired to be able to observe the processing field during application of the laser radiation. This holds true, in particular, for the aforementioned LASIK method wherein the treating physician has to observe the field of operation. Therefore, the aforementioned laser processing device usually comprises an optical system for imaging the area to which the laser radiation is applied. The image is generated either on a camera or in an intermediate image plane from which direct visual inspection through an eyepiece is then possible. Observation is effected through the central region of the adapter, and it is required for the laser processing device to illuminate the area to which the laser radiation is being applied and which is being observed as the object field.

Since the adapter usually contacts the object to be processed, it is generally required to employ a separate fresh adapter for each object. This is necessary, in particular in ophthalmic methods, under the aspect of sterility. As a consequence, a fresh adapter has to be fixed to the laser processing device, which is then provided as a therapeutic appliance, every time before processing or before surgery. For fixation, it is known from WO 03/002008 A1 to hold the contact glass in a forceps-like means which is locked on the laser processing device. Locking thereof is effected by a collar guided along a rail. The adapter is pushed in transverse to the optical axis in a form-locking manner.

DE 19 831 674 A1 describes the use of a mechanical coupling mechanism wherein a metal rod fixed to a mount of a contact glass at an oblique angle is held in a sleeve by means of a magnet or a solenoid. The sleeve itself is fitted onto a mechanical adjustment mechanism such that the position of the contact glass can be adjusted.

The prior art solutions for the contact glass realizing an adapter all require, on the one hand, a large number of components that are complicated to manufacture and, on the other hand, the fixations used in the prior art lead to units having relatively large structural dimensions. This makes prior art contact glasses disadvantageous for devices which are to be used on a patient without general anesthesia, but only with local anesthesia. The large amount of material required to produce this disposable article is also a disadvantage, in particular under economic and ecological aspects.

SUMMARY OF THE INVENTION

Therefore, it is the object of the invention to structurally simplify an adapter of the aforementioned type in terms of its fixation to the laser processing device so that, in particular, an application without general anesthesia is also possible. In particular, an application should be possible in which the adapter is used, already completely fixed to the laser processing device, on the locally anesthesized patient.

According to the invention, this object is achieved by an adapter of the type mentioned above, wherein fixing means are provided at the peripheral region, said means allowing the adapter to be releasably fixed to a receiving part of the laser processing device such that, upon application of a determined pulling force along the optical axis, the fixing means are removable from said receiving part According to the invention, the object is also achieved by an adapter of the type mentioned above, which is fitted on and removable from a receiving part of the laser processing device by an axial movement (with respect to the optical axis), being fixed in particular by vacuum.

The fixation of the adapter according to the invention to a receiving part of the laser processing device thus allows to fit the adapter on the laser processing device and to remove it therefrom again by an axial movement (with respect to the optical axis). This approach is based on the finding, first made by the inventors and not mentioned in the prior art, that there may sometimes be panic-like attempts by the patient to move his head away from the laser processing device provided as a therapeutic appliance when using an adapter for an ophthalmic method without general anesthesia. The adapter according to the invention has the advantageous properties of a "panic lock" which opens when the head is being pulled away from the therapeutic appliance.

Nevertheless, the adapter is surprisingly easy to realize by providing the fixing means at the peripheral region of the adapter which is not located in the beam path of the laser processing device during use of the adapter.

The adapter according to the invention allows an easy-to-establish connection to the laser processing device, not requiring complex insertions and adjustments such as those which are indispensable in the prior art. In particular, it is not mandatory to effect fixation with the adapter positioned at a certain angle, as is indispensable, for example, in the magnetically operating sleeved of DE 19 831 674 A1.

Moreover, the adapter according to the invention can be removed again from the laser processing device in a particularly quick and simple manner, and the connection opens in particular in cases of panic where a certain pulling force along the optical axis is exceeded. Finally, the adapter according to the invention achieves the desired compact structure.

The compact design which is possible for the adapter according to the invention surprisingly turns out to be advantageous also for psychological reasons when used in ophthalmic methods. Due to the relatively small adapter to be placed on the patient's eye, patients will from now on consider the operation to be considerably less dangerous or threatening, so that the occurrence of situations of panic, in which the panic lock property of the adapter would be effective, is considerably reduced.

The provision of the fixing means contacting the peripheral region may be effected in multiple ways in connection with the invention. Thus, mechanical, electrical or pneumatic principles of operation are equally suitable.

For mechanical fixation, for example, tongues may be used which engage the receiving part of the laser processing device. The tongues are advantageously designed such that the adapter is simply fitted into or onto the receiving part. Particularly advantageously, in order to ensure secure locking, a snap-fit mechanism in which the tongues snap into the receiving part may be used in addition to a friction contact formed by the tongues with the receiving part. For example, this snap-fit mechanism may be provided with a snap-fit nose. In order to remove the adapter, i.e. to release the fixing means from the receiving part, the snap-fit noses then have to be pulled out of the receiving part. The force necessary to remove the adapter may be set by a suitable design of snap-fit noses and recesses retaining said snap-fit noses. As an alternative or in addition, all or some of the tongues may also be dimensioned such that they break upon application of the determined pulling force. This embodiment has the additional advantage that the adapter can be used only once. Thus, it is easy for the user to comply with the requirements of sterility.

In order to set a determined pulling force, inclined surfaces may be used, for example, for the snap-fit noses or the recesses, so that the determined pulling force can be set by selecting the angle at which the inclined surfaces extend.

Of course, the concept of tongues and receiving part can also be inverted, i.e. the peripheral region comprises a receiving part for tongues located on the laser processing device.

An example of pneumatic fixation consists in providing a flange surface for vacuum fixation. For this purpose, the adapter may be inserted into a bore comprising a stop in the form of a step-like taper. By applying a negative pressure (vacuum) to the side of the adapter located on the side of the microscope device, the adapter is pulled onto the stop in the bore and is held there. Using this concept, a certain centering of the adapter is achievable at the same time. Therefore, it is preferred that the fixing means comprise a flange surface provided on the adapter for vacuum fixation. This is an example of a design in which the fixing means align the central region of the adapter with the optical axis of the laser processing device. In this case, it is particularly preferred to design the flange surface such that it has a small vacuum leakage rate. This makes it possible to generously tolerate the surfaces and to produce them at low cost. In this case, the vacuum pump is dimensioned such that it maintains a sufficient vacuum in spite of or at a given leakage rate.

If it is desired to enhance the centering effect of the fixation, the peripheral region of the adapter may be provided with a frustoconical shape. The bore then also needs to have a conical design, so that the frustoconical adapter is pulled into the tapered bore by the vacuum.

In an alternative embodiment of this self-centering fixing mechanism, the peripheral region of the adapter may conically expand towards the laser processing device. If the laser processing device comprises a matching frustoconical receiving part, the adapter can then also be easily fixed to the laser processing device in a centering manner by means of suction.

The designs described with respect to vacuum fixation may, of course, be used also when using appropriate materials to take advantage of electromagnetic or electrostatic effects.

In order to improve the optical properties of the adapter, it may be useful in some cases to employ liquid contact agents at the optical interfaces of the adapter. This principle of immersion optics known in microscopy improves the adhesive and optical properties of the adapter.

As already mentioned, a field of application for the adapter in which the advantages of the adapter are particularly effective is ophthalmic surgery. Therefore, it is preferred to provide the central region of the adapter as a contact glass to be placed on the object, in particular the cornea of the eye. For such a contact glass, the peripheral region may be conveniently designed as a mount.

Depending on the method of manufacture and the materials used, the central region and the peripheral region may be integrally formed. When using a plastic material, an injection molding method, for example, is then suitable for manufacture.

In order to ensure the desired secure mechanical coupling between the object and the laser processing device, it is advisable to not only place the adapter in contact with the object, but also to fix it thereto. In order for the central region that comes to lie in the beam path of the laser processing device to be affected as little as possible in its optical function, it is thus convenient to provide the necessary fixing means for fixation to the object at the peripheral region. The fixing means—in the case of ophthalmic methods a suction duct structure for fixation by vacuum is suitable here, for example—then place the central region in contact with the object.

BRIEF DESCRIPTION OF THE DRAWINGS

The invention will be explained in more detail below with reference to the drawings, wherein.

DETAILED DESCRIPTION OF THE DRAWINGS

Figure 1:
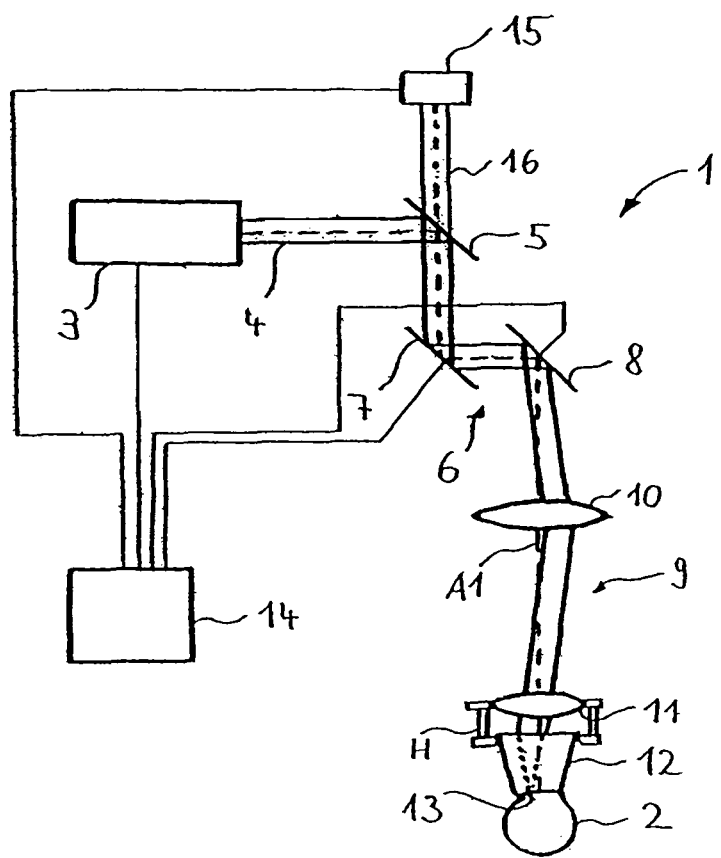
FIG. 1 shows a schematic view of a laser processing device for an ophthalmic method.

FIG. 1 shows a treatment apparatus for an ophthalmic method similar to that described in EP 1 159 986 A1 or in U.S. Pat. No. 5,549,632. The treatment apparatus 1 of FIG. 1 serves to effect correction of defective eyesight on the eye 2 of a patient according to the known LASIK method. For this purpose, the treatment apparatus 1 comprises a laser 3 which emits pulsed laser radiation. The pulse duration is e.g. in the femtosecond range, and the laser radiation acts by means of non-linear optical effects in the cornea in the manner described above. The treatment beam 4 emitted by the laser 3 along an optical axis A1 is incident on a beam splitter 5 which guides the treatment beam 4 to a scanning unit 6. The scanning unit 6 comprises two scanning mirrors 7 and 8 which are rotatable about mutually orthogonal axes such that the scanning unit 6 two-dimensionally deflects the treatment beam 4. Adjustable projection optics 9 focus the treatment beam 4 onto or into the eye 2. The projection optics 9 comprise two lenses 10 and 11. The treatment apparatus 1 represents a laser processing device.

Following the lens 11, there is arranged an adapter 12 which is permanently connected to the lens 11, and thus to the beam path of the treatment apparatus 1, by a holder H. The adapter 12, which will be described in more detail later, contacts the cornea of the eye 2. The optical combination of the treatment apparatus 1 with the adapter 12 attached to it causes the treatment beam 4 to be focused in a focus 13 located in the cornea of the eye 2.

Like the laser 3 and the projection optics 9, the scanning unit 6 is also controlled by a control apparatus 14 via control lines (not specified in detail). The control apparatus 14 determines the position of the focus 13 both transverse to the optical axis A1 (through the scanning mirrors 7 and 8) and along the optical axis A1 (through the projection optics 9).

The control apparatus 14 further reads out a detector 15 which reads out radiation scattered back by the cornea and passing through the beam splitter 5 as back reflection radiation 16. The detector 15 allows very exact control of the operation of the laser 3.

The adapter 12 ensures that the cornea of the eye 2 obtains a desired intended shape. Due to the cornea 17 contacting the adapter 12, the eye 2 is in a predetermined position to the adapter 12 and thus to the treatment apparatus 1 connected to it.

Figure 2:
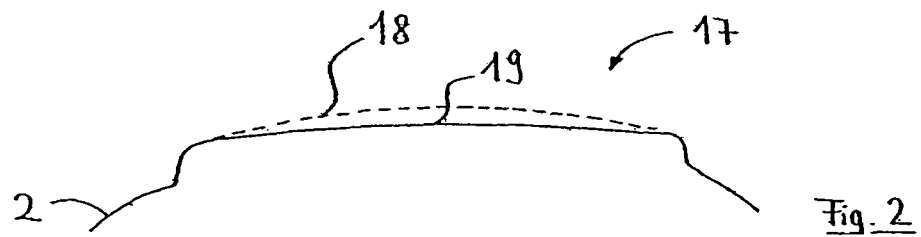
FIG. 2 shows a schematic view of a patient's cornea.

This is schematically shown in FIG. 2, which shows a sectional view of the cornea 17. In order to achieve exact positioning of the focus 13 in the cornea 17, the curvature of the cornea 17 has to be taken into account. The cornea 17 has an actual shape 18 which differs from one patient to another. Now, the adapter 12 contacts the cornea 17 such that it deforms the latter toward a desired intended shape 19. The exact profile of the intended shape 19 depends on the curvature of that surface of the adapter 12 which faces the eye 2.

Known geometric and optical conditions for introducing and focusing the treatment beam 4 in the cornea 17 are given by the adapter 12. Since the cornea 17 is in contact with the adapter 12, which is in turn stationary relative to the beam path of the treatment apparatus 1 due to the holder H, the focus 13 can be exactly positioned three-dimensionally in the cornea 17 by the control of the scanning unit 6 and the adjustable projection optics 9.

Figure 3:
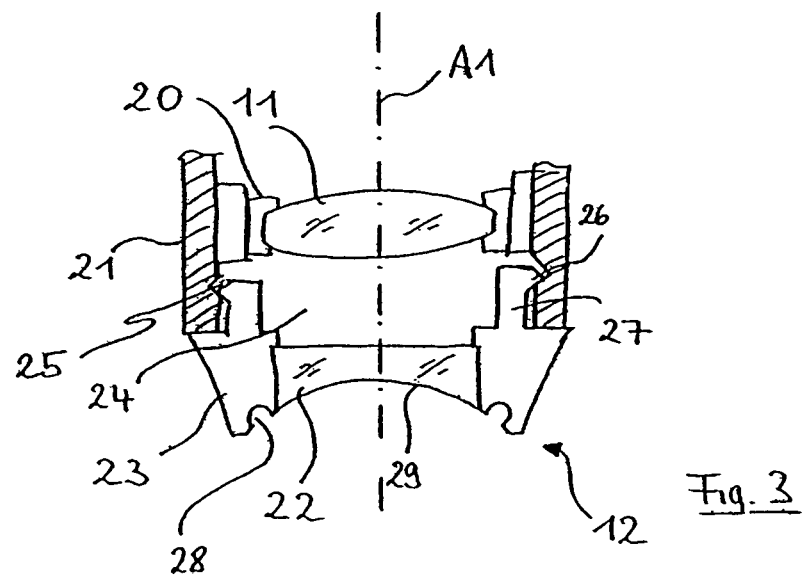
FIG. 3 shows a sectional view of a contact glass for the laser processing device of FIG. 1 and a schematic view of the fixation of the adapter.

FIG. 3 shows a detail of the holder H of the adapter 12. As can be seen, the foremost lens 11 of the treatment apparatus 1 is located in a lens mount 20, which is in turn arranged in a cylindrical receiving part 21.

The adapter 12 has a two-part structure and consists of a contact glass 22 glued into a mount 23. By sucking the mount 23 onto the cornea 17, the lower side 29 of the contact glass 22 glued into the mount 23 is pressed onto the cornea 17 such that the cornea's desired intended shape 19 already explained above is ensured.

Instead of the two-part design according to FIG. 3, the adapter 12 may also be integrally designed. The mount 23 and the contact glass 22 are thus manufactured from one continuous part, e.g. by an injection molding method or by a machining method from a single unmachined part. In principle, the presently described variants of the adapter 12 may be realized in multi-part form or in single-part form, in particular where the contact glass 22 and the mount 23 are concerned.

The receiving part 21 is provided as a bore 24 on the inside of which an annular groove 25 is formed. The diameter of the bore 24 is dimensioned such that the cylindrical collar on the mount 23 can be pushed into the bore 24.

Figure 4:
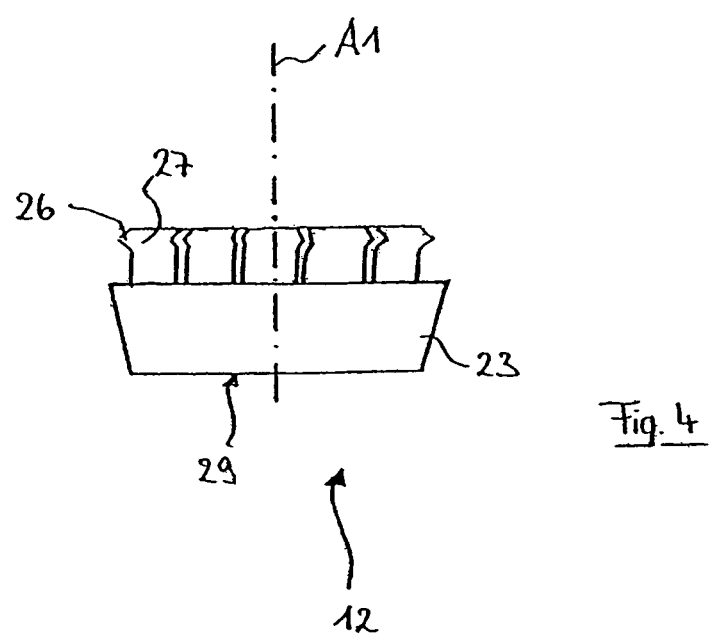
FIG. 4 shows a lateral view of the adapter of FIG. 3.

Noses 26 of tongues 27 engage with the groove 25, said noses being formed by the tubular collar provided on the treatment-side end of the mount 23. As the lateral view of the adapter 12 shown in FIG. 4 shows, the tongues are formed by cutouts in the tubular collar. The tongues 27 are thus flexible and can be bent inwards when pushing the tongues into the bore 24.

As the noses 26 pass into the groove 25, the tongues 27 spring back and the mount 23 with the contact glass 22 is held in the receiving part 21.

Instead of the groove 25, a suitable recess or a suitable extension may be provided in the receiving part 21.

The axial position, i.e. the position on the optical axis A1, is defined by a flange (not specified in detail in FIG. 3) serving as a stop, which is drawn to a corresponding mating surface of the receiving part 21. Due to the fixation, the contact glass is aligned with the optical axis A1; the same goes for a cornea 17 pressure-contacted by the lower side 29 of the contact glass 22 by means of the suction duct 28.

In the fixed state, the noses 21 hook into the groove 25. The mount 23 with the contact glass 22 is thus fixed and can no longer be pulled out of the receiving part 21 without an additional amount of force. Considerably more force has to be applied for removing it than for pushing it in. This may even be enhanced by a suitable design of an introducing cone at the front edge of the receiving part 21, which front edge faces away from the lens 11. The force required in order to remove the adapter 12 can be set by the sides of the noses 26 that are located away from the lens 11. In the exemplary embodiment of FIG. 3, inclined surfaces are provided there. By selecting the angle of said inclined surfaces, the force required to pull the adapter 12 out is set.

If it is desired to achieve a great minimum pulling force for removal of the adapter 12 from the receiving part 21, the lower side of the noses 26 may be suitably designed in order to achieve a form-locking connection.

In addition, one or more of the tongues 27 may be provided such that they break when pulling the mount 23 out of the receiving part 21. This may be achieved, for example, by a breaking point located on a tongue 27. This approach allows to efficiently avoid multiple use of a contact glass 22 with the mount 23 where one-time use is prescribed, for example, for reasons of sterility.

The concept of tongues 27 and noses 26 may, of course, be inverted such that the noses 26 are located inside with respect to the optical axis A1. The receiving part 21 should then not be provided as a bore 24, but as an outside circular cylinder whose groove 25 is then formed on the outside. The mount 23 is then pushed over the receiving part 21.

Of course, the concept of tongue and receiving part may also be interchanged so that the tongues are provided on the treatment apparatus 1 and the receiving part is provided on the mount 23.

Figure 5:
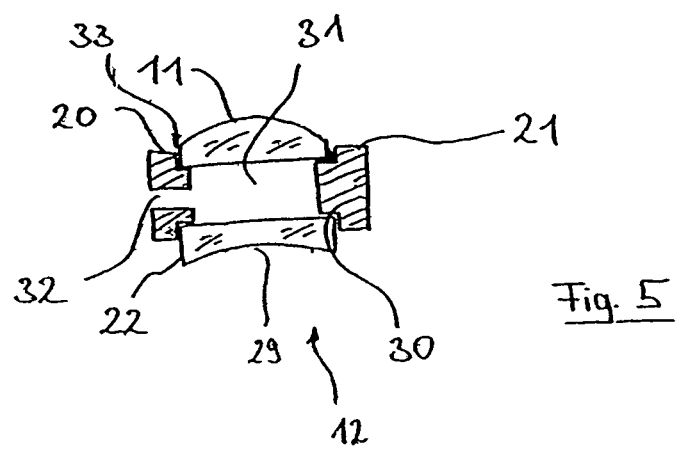
FIG. 5 shows a sectional view of a differently designed adapter which is fixed by vacuum.

FIG. 5 shows a different embodiment of the adapter 12. Here, the adapter 12 is provided as a contact glass 22 without a mount and is pushed into a receiving part 21 having at its lower end, i.e. the side facing away from the lens 11, a step extending around the inner circumference. In this embodiment, the receiving part 21 is part of the lens mount 20 which continues as a tubular shape below the lens 11.

This provides a stop up to which the contact glass 22 can be pushed into the adapter 12. Thus, the contact glass 22 abuts against an annular peripheral region at the stop surface 30 formed in the receiving part 21. The contact glass 22, the receiving part 21 as well as the lens 11 form a cavity 31 which can be evacuated via a lateral suction port 32. For improvement of air-tightness or for a reduction of the required suction power, the lens 11 is inserted into its mount 20 in a sealing manner additionally by means of a seal, e.g. by a sealing ring, or by means of an adhesive bond 33.

Thus, held by vacuum, the contact glass 22 is supported by its annular peripheral region on the stop surface 30. At the same time, centering of the contact glass is achieved by the bore in the receiving part 21. If it is desired to enhance this centering even more, the peripheral region of the contact glass 22 may be provided with a frusto-conical design and the bore in the receiving part 20 is given a corresponding tapered cone shape.

Figure 6:
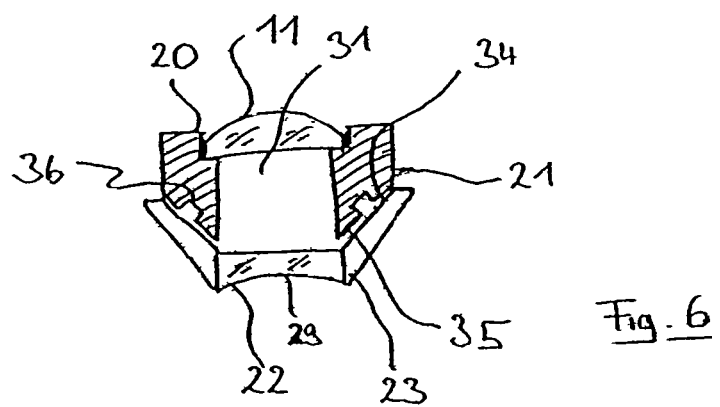
FIG. 6 shows a further adapter to be fixed by vacuum.

The principle of self-centering is utilized in a different manner in the construction of FIG. 6. Here, the contact glass 22 is held in a mount having a conical flange surface 34 which expands towards the treatment apparatus 1. The receiving part 21 comprises a corresponding mating surface as a contact surface 35. In this conical contact surface 35, a circumferential milled slot 36 is provided which is connected to a suction line (not shown). By means of a vacuum, the mount 23 with its flange surface 34 is drawn onto the contact surface 35 and, thus, the contact glass 22 is centered at the same time.

In order to achieve a particularly good vacuum build-up, it is advantageous to provide the mount 23 with a flexible material, such as silicone, for example, at least at the flange surface 34, because such a material leads to particularly good air-tightness and, thus, to a very good retaining force. Of course, this measure may also be employed in the embodiment of FIG. 5.

Figure 7:
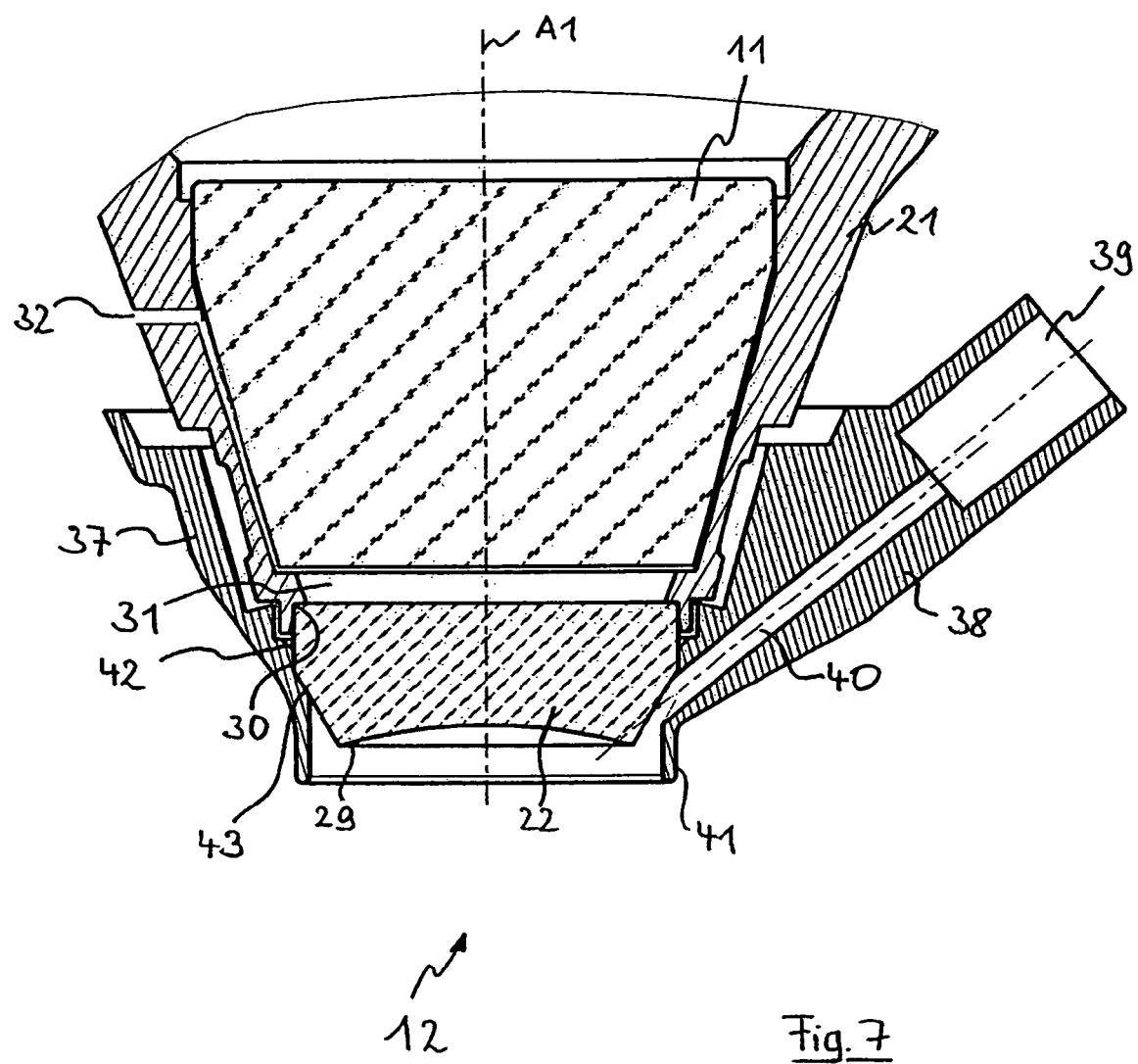
FIG. 7 shows a further embodiment of the adapter of FIG. 5.

FIG. 7 shows an adapter 12 which adopts the fixing principle of the adapter of FIG. 5. Like elements are provided with the same reference numerals so that, in this connection, reference is also made to the description of FIG. 5. However, as a modification of the construction of FIG. 5, the contact glass 22 is provided with a contact glass holder 37 serving as the mount.

The contact glass 22 is located in the contact glass holder 37. It comprises a conical portion which tapers towards the eye and contacts a conical annular surface 43 of the contact glass holder 37. In order to fix the contact glass 22 in the contact glass holder 37, adhesive bonding may be effected in this place. As an alternative or in addition, adhesive bonding is possible in the region of the cylindrical portion of the contact glass. For this purpose, the contact glass holder 37, constructed according to FIG. 7, conveniently has a suitable conical bevel into which adhesive is introduced after placing the contact glass 22 in the contact glass holder 27, so that the contact glass holder 37 is fixed to the contact glass 22.

The contact glass holder 37 does not contribute to the fixing of the contact glass 22 which, as in the construction of FIG. 5, is also drawn to the stop surface 30 by means of a vacuum with an annular peripheral region of the upper surface, i.e. the surface facing the laser processing device. The vacuum in the cavity 31 is in turn applied via a suction line 32 provided as a duct through the receiving part 21 of the treatment apparatus 1. The duct may be formed in the receiving part 21 which is funnel-shaped in the exemplary embodiment of FIG. 7. It is also possible to design the duct by a corresponding groove in the receiving part 21 such that it is limited by the funnel-shaped receiving part 21 and the inserted foremost lens 11. Since the lens 11 is in turn fixed in the receiving part 21 in a sealing manner, e.g. by gluing, the application of a vacuum through the suction line 32 leads to evacuation of the cavity 31, which draws the contact glass 22 onto the stop surface 30. Opening of this vacuum fixation is achieved with a force which overcomes the suction force exerted by the vacuum fixation. Setting the suction power at the suction line 32 allows the force needed to remove the contact glass 22 from the stop surface 30 to be set as desired to obtain a panic lock function.

The means for centering the contact glass 22 are provided as a fit here, by way of example, which fit is formed by a cylindrical collar that extends from the stop surface in a manner parallel to the optical axis A1 and into which fit the contact glass 22 is introduced in an axial direction towards the stop surface 30 during fixation.

In order to fix the contact glass 22 to the object, i.e. to the eye, the contact glass holder 37 comprises a stud 38 having a Luer lock fitting 39 as well as a suction duct 40 connected with it. The suction duct 40 laterally terminates at the contact glass 22 above a check ring 41 of the contact glass holder 37, which ring axially protrudes relative to the lower side 29 of the contact glass 22. During fitting of the contact glass 22, this check ring first contacts the cornea 17. Then, the unit consisting of the contact glass holder 37 and the contact glass 29 is drawn towards the eye by application of a vacuum to the Luer lock fitting 39, so that the lower side 29 of the contact glass ensures the desired intended shape 19 of the cornea 17 as already explained.

Since the vacuum conditions during suction of the contact glass 22 onto the cornea 17 may vary much stronger than the pressure conditions in the cavity 31, it is preferred to make the vacuum fixation of the contact glass 22 with the contact glass holder 37 to the eye much stronger than the vacuum fixation of the contact glass 22 to the stop surface 30. When the eye is released from the treatment apparatus 1 due to panic, the connection between the contact glass 22 and the receiving part 21 opens with a very precisely adjustable or adjusted force; the contact glass 22 itself with the contact glass holder 37 remains on the eye.

The invention claimed is:

1. An adapter for mechanically coupling a receiving part of a laser processing device to an object, said adapter comprising:
a contact glass movable into a beam path of the laser processing device, wherein the beam path extends to an object along an optical axis, said contact glass having an upper surface and an annular peripheral region and
said adapter fixable to the laser processing device and provided so as to contact the object with said contact glass such that the upper surface is facing the laser processing device, and wherein fixing means allow such adapter to be releasably fixed to the receiving part of the laser processing device such that, upon application of a designed and predetermined pulling force along said optical axis, said adapter with the fixing means are completely detachable from said receiving part without damage to the receiving part,
said fixing means is provided by the upper annular peripheral region of the upper surface of the contact glass, said upper annular peripheral region engageable with a stop surface of the receiving part, and wherein fixing means are provided for fixation by a vacuum, the vacuum provided above the upper surface of the contact glass between the contact glass and the receiving part.

2. The adapter as claimed in claim 1, in combination with the laser processing device.

3. An adapter for mechanically coupling a laser processing device to an object, the laser processing device having a receiving part, said adapter comprising:
a central region movable into a beam path of the laser processing device, wherein said beam path extends to an object along an optical axis, and
a peripheral region located outside said central region, wherein at said peripheral region, a flange surface is provided for vacuum fixation of the adapter to a stop surface on the receiving part of the laser processing device when a vacuum is applied intermediate the adapter and the receiving part,
said adapter fixable to the laser processing device and being provided so as to contact the object with said central region, and wherein said vacuum fixation of the adapter to a stop surface allows the adapter to be releasably fixed to the receiving part such that the adapter is completely releasable from the receiving part without damage to the adapter or receiving part of the laser processing device and such that such adapter can be inserted into said receiving part by an insertion movement extending substantially along said optical axis prior to each laser procedure and removed following each laser procedure.

4. The adapter as claimed in claim 3, wherein said vacuum fixation aligns said central region with said optical axis.

5. The adapter as claimed in claim 3, wherein said central region is provided as a contact glass to be placed on the object.

6. The adapter as claimed in claim 3, wherein said peripheral region and said central region are integrally provided and comprise a polymer.

7. The adapter as claimed in claim 3, in combination with the receiving part of the laser processing device.

8. The adapter as claimed in claim 3, further comprising frangible portions that break upon release of the adapter from the receiving part by the application of the designed and predetermined pulling force whereby the breakage of the frangible portions prevents reuse of the adapter.

9. An adapter for mechanically coupling a laser processing device to an object, said adapter comprising:
a central region selectively movable into a beam path of the laser processing device having a receiving part, the beam path extending to an object along an optical axis; and
a peripheral region outside of said central region comprising fixing means enabling the adapter to be releasably fixed to said receiving part, such that said fixing means is fitted on to the receiving part prior to each laser processing procedure and the fixing means and adapter are completely detachable from said receiving part upon application of a designed, predetermined pulling force along said optical axis without damage to the receiving part,
said fixing means comprises at least one of the following set:
a) a plurality of tongues;
b) a flange of surface for vacuum fixation, and wherein the receiving part having a stop surface whereby when vacuum is applied intermediate the adapter and the receiving part the adapter is drawn onto the stop surface and the vacuum fixation is provided,
c) frustoconical surface that confronts a. cooperating frustoconical surface of the receiving part, and
d) a snap-fit mechanism.

10. The adapter of claim 9, in combination with the laser processing device.

11. The combination of claim 10, wherein the central region is configured as a contact glass with a concave surface for engaging the object and the peripheral region comprises a contact glass holder.

12. The adapter of claim 9, wherein said fixing means align said central region with said optical axis.

13. The adapter of claim 9, wherein said central region is provided as a contact glass to be placed on the object.

14. The adapter of claim 13, wherein said peripheral region is designed as a mount of said contact glass.

15. The adapter of claim 9, wherein said peripheral and central regions are integral.

16. The adapter of claim 9, wherein said fixing means is provided at said peripheral region for holding said central region in contact with the object.

17. The adapter as claimed in claim 9, further comprising frangible portions that break upon release of the adapter from the receiving part by the application of the designed and predetermined pulling force whereby the breakage of the frangible portions prevents reuse of the adapter.

18. An adapter for mechanically coupling a laser processing device to an object, said adapter comprising:
a central region movable into a beam path of the laser processing device, wherein the beam path extends to an object along an optical axis, and
a peripheral region located outside said central region, wherein fixing means are provided at said peripheral region, said adapter fixable to the laser processing device and provided so as to contact the object with said central region, and wherein said fixing means allow the adapter to be fitted on prior to each laser processing procedure and upon application of a designed and predetermined pulling force along said optical axis, said fixing means are detachable from said receiving part releasing said adapter from the laser processing device without damage to the receiving part,
said fixing means comprising at least one of the following set:
a) a plurality of tongues;
b) a flange surface for vacuum fixation, and wherein the receiving part having a stop surface whereby when vacuum is applied intermediate the adapter and the receiving part the adapter is drawn onto the stop surface and the vacuum fixation is provided,
c) a frustoconical surface that engages a cooperating frustoconical surface of the receiving part, and
d) a snap-fit mechanism.

19. The adapter as claimed in claim 18, wherein said central region is provided as a contact glass and the fixing means comprises the flange surface for vacuum. fixation and wherein the receiving part has the stop surface, and wherein the flange surface is an annular peripheral region on a top surface of the contact glass.

20. The adapter as claimed in claim 18, wherein the peripheral region is provided as a contact glass holder and said contact glass holder has a suction duct in communication with a region below the contact glass for vacuum attachment of the contact glass to the object.

\* \* \* \* \*

UNITED STATES PATENT AND TRADEMARK OFFICE
CERTIFICATE OF CORRECTION

| | | |
|---|---|---|
| PATENT NO. | : 8,425,494 B2 | Page 1 of 1 |
| APPLICATION NO. | : 10/579645 | |
| DATED | : April 23, 2013 | |
| INVENTOR(S) | : Dirk Muhlhoff et al. | |

It is certified that error appears in the above-identified patent and that said Letters Patent is hereby corrected as shown below:

On the Title Page, Item (57) in the Abstract, line 12, delete "The" and insert --the--

In the Claims

Col. 10, line 18, delete "a." and insert --a--

Col. 11, line 3, delete "vacuum." and insert --vacuum--

Signed and Sealed this
Twenty-sixth Day of November, 2013

Margaret A. Focarino
*Commissioner for Patents of the United States Patent and Trademark Office*